United States Patent [19]
Peters

[11] 4,287,891
[45] Sep. 8, 1981

[54] SECURING DEVICE FOR SURGICAL TUBES

[76] Inventor: Joseph L. Peters, 282B Ballard La., Finchley, London N.12, England

[21] Appl. No.: 71,484

[22] Filed: Aug. 31, 1979

[51] Int. Cl.³ .............................................. A61B 17/34
[52] U.S. Cl. .................................. 128/34.; 128/348; 128/DIG. 26
[58] Field of Search ...................... 128/1 R, 348–350, 128/DIG. 26; 24/16 PB, 17 B, 68 C, 69 R

[56] References Cited

U.S. PATENT DOCUMENTS

| | | | |
|---|---|---|---|
| 2,820,457 | 1/1958 | Phillips | 128/DIG. 26 |
| 3,730,187 | 5/1973 | Reynolds | 128/DIG. 26 X |
| 3,765,420 | 10/1973 | Felczak | 128/347 |
| 3,783,876 | 1/1974 | Dye | 128/348 X |

Primary Examiner—Stephen C. Pellegrino
Attorney, Agent, or Firm—Watson, Cole, Grindle & Watson

[57] ABSTRACT

A surgical safety device to be fixed externally to the body of a patient fitted with a body tube for securing the body tube against unintentional displacement into or out of the patient, comprises two relatively rotatable tubular members telescoped together and defining a bore for receiving the body tube, and an elongate flexible element located in the bore and having its opposite ends fixed to the respective members. When the tubular members are rotated the flexible element wraps itself around the tube and grips it to prevent longitudinal displacement through the safety device.

9 Claims, 4 Drawing Figures

SECURING DEVICE FOR SURGICAL TUBES

This invention is concerned with surgical equipment and methods used in hospitals.

In the treatment of patients it is not uncommon for tubes to be inserted into the body of a patient, either through an existing body orifice or an opening specially provided. Such tubes are referred to generally as body tubes and specific examples of such tubes include catheters or cannulae used for blood or other administration purposes, drainage tubing introduced into body cavities, especially after operations, for draining off fluids, and naso-gastric tubes. It is normal practice for body tubes to be secured to the patients skin outside of the body in order to avoid any inadvertant displacement of the tube either into or out of the body. Such securement is, in some cases, achieved simply by means of a strip of adhesive tape whereas in other cases a bandage may be used.

It is especially important that drainage tubes, for example inserted through wounds into thoracic or abdominal cavities, should be securely held against unintentional movement either into the body or out of it. Different techniques have been used for this purpose and include stitching the tubing to the skin of the patient at the location where it emerges through the wound, wrapping a thread stitched to the patient around the tubing several times to grip and hold the tubing, and attaching a safety pin to the patients skin by loops of thread and then pushing the safety pin laterally through the tube wall. These known methods have several disadvantages, but the main drawback is that adjustments of the surgical drains, for example by shortening the length of tube located within the body, are difficult and time consuming because of the manipulations required, and as a result can be painful to the patient. The fact that there is not a standard technique used by all surgeons who instead are guided by personal preferences does not ease the tasks of nurses who have to perform adjustments later.

The present invention aims at providing a solution to the problems associated with securing body tubes and broadly resides in a tubular device, to be fixed externally to the body of a patient fitted with a body tube, the body tube passing through the device which is adjustable either to grip the tube securely or to release the tube to allow the tube to be pulled freely through the device.

The adjustment of the device may be a simple operation, for example relative rotation or axial movement of two tubular parts making up the device, which, when the device is fitted to a drainage tube for example, facilitates any necessary re-positioning of the tube which is achieved simply by adjusting the device to release the tube, pulling the tube through the device to the new position, and retightening the device.

Drainage tubes are normally flexible and made of plastics material or rubber, especially silicone rubber, with the consequence that they can be easily crushed or pinched to close the central passageway.

A preferred form of device according to the invention is suitable for use with such tubes and is constructed so as to avoid the device exerting too strong a constricting or clamping action on the tube while still gripping the tube securely enough to prevent any movement of the tube through the device. To be more specific the device comprises two relatively rotatable tubular members telescoped one inside the other, and an elongate flexible element positioned within the tubular member and having its opposite ends fast for rotation with the respective members. When the members are rotated with respect to each other the elongate element wraps itself onto a tube passing through the device and securely holds the tube. Means, preferably in the form of a ratchet, are provided for locking the members releasably in their adjusted angular positions with respect to each other.

The device can, of course, take other forms and in a particularly simple construction comprises two tubular parts screw threaded together and adjustable relative to each other to deform a tube gripping element interposed between them radially inwards for gripping a tube.

Another form of device which is envisaged consists of a first tubular part having a plurality of axially extending integral fingers adapted to be deflected inwardly by a second part to grip a tube passed through the device. The second part is preferably adjustable between several positions so as to deflect the fingers by varying amounts for gripping different diameter tubes.

The invention also resides in a method of securing a surgical body tube externally of a patient comprising the steps of providing a tubular safety device capable of adjustment either to grip frictionally or to release a tube passed through the device, passing the tube through the safety device, attaching the device to the body of the patient, and adjusting the device to grip securely the tube without collapsing the tube and closing its interior passage.

One particular form of safety device embodying the invention will now be described by way of example with reference to the accompanying drawing, in which.

Figure 1:
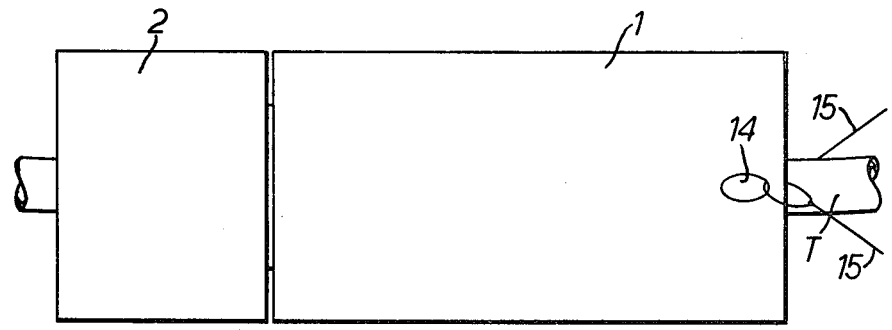
FIG. 1 is a side view of the device.

The safety device illustrated in the drawings is tubular and includes front and rear main parts 1 and 2, respectively, which are cylindrical and coaxial. The front part 1 has an axial bore 3 and a counterbore into which a forwardly protruding boss 4 of the rear part extends. The rear part 2 has an axial bore 5 which aligns with the bore 3 of part 1 and an elongate gripping element 6 of flexible and slightly elastic material is accommodated within the bores 3,5. The element 6 has tubular end portions 7,8 which are fixed firmly to the opposed ends of parts 1,2 by force-fitted sleeves 9,10 which clamp the end portions against the walls of bores 3,5. The end portions of the gripping element are interconnected by a plurality, four as shown, of integral strips 11. Thus the gripping element has the form of a tube with four longitudinal slots cut in its wall.

The internal shoulder formed in front part 1 and the forward end of the boss 4 are provided with ratchet teeth 12,13 which cooperate to permit relative rotation between the front and rear parts 1,2 in one direction only. At its forward and the front part 1 is provided with holes 14 for thread 15 by means of which the device can be attached to the body of a patient.

Figure 2:
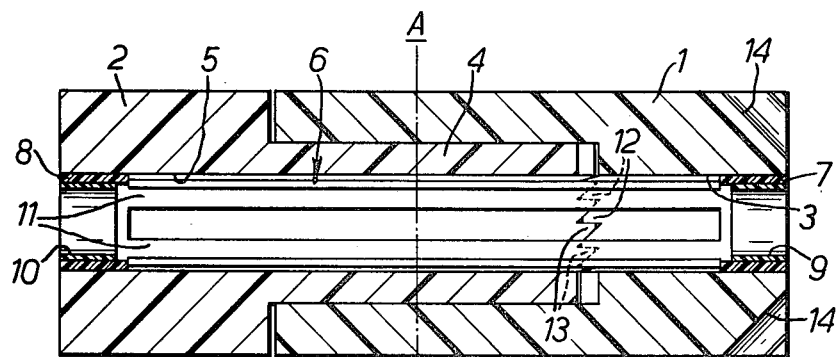
FIG. 2 is an axial section through the device.
Figure 3:
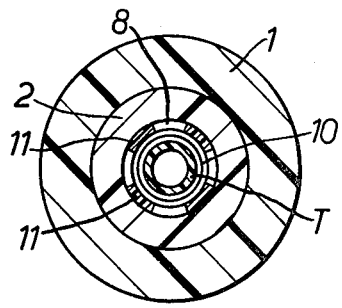
FIG. 3 is a transverse cross-section taken along the line A—A in FIG. 2.
Figure 4:
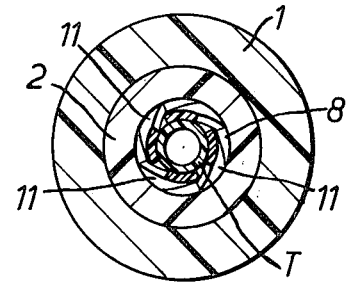
FIG. 4 is the same section as FIG. 3, but showing the device adjusted to grip a tube.

In use of the device, with the device adjusted as seen in FIGS. 2 and 3, the body tube, for example surgical drainage tube T, to be secured is passed through the device. The forward end of the device is then attached to the patients body by thread 15 passing through holes 14 and stitched to the skin. The device is adjusted to grip firmly the tube T by relatively rotating the front and rear parts 1,2 in the direction permitted by the ratchet teeth 12,13. Because the ends of the gripping element 6 are fast with the respective parts 1,2, the relative rotation between them causes the element to twist so that the strips 11 tend to wind up to extend along generally helical paths and move inwardly to grip the tube T (FIG. 4). The strips 11 engage the tube over a substantial length, for example approximately 4 cms, which means that the tube can be held firmly without being crushed or pinched closed. When the device has been tightened the correct amount, the ratchet teeth 12,13 prevent it loosening.

If, subsequently, it is desired to adjust the position of the tube, such as to shorten the drain, to release the tube the front and rear parts 1,2 are pulled axially apart to disengage the ratchet teeth 12,13 and are then turned to loosen the gripping element 6. The tube T can be pulled easily through the device for adjusting its position, after which the device can be tightened again, as described above, to secure the tube once more.

It is to be noted that as the strips 11 are twisted they tend to draw together axially the parts 1,2 bringing the ratchet teeth into tighter engagement and thereby making the device more secure against inadvertent loosening of the tube. Of course, means other than the ratchet teeth could be provided for locking the two parts 1,2 in their adjusted positions.

The described safety device can be used with tubes of different diameters and the two parts 1,2 could be provided with registration marks which would indicate at a glance when the device had been adjusted correctly for each tube diameter. Alternatively the device could be intended for use with one size tube only and be provided with means to limit positively the permitted rotation between parts 1 and 2.

The front and rear parts of the device are conveniently moulded from plastics material and, if required either or both, could be provided with means to assist attachment of the device to a patient, for example a flange plate which could be held in place on the body by a strip of adhesive tape.

Alternatively or additionally a groove could be provided around the periphery of the device for receiving a strap, such as a velcro strap, to be wrapped around a limb of the patient for attaching the device thereto.

The inner gripping element 6 of the inventive device has been described and illustrated as having its ends fastened to the main, outer ports 7,2 by force fitted sleeves. However, it will be recognised that other means could be used. For example, the element could be provided with external flanges at its ends which are received in shallow counterbores in the outer ends of the parts 1,2 and have a splined connection with the ports 1,2 making its opposite ends fast with the respective parts. The splines could conveniently be formed on the flangers.

Other modifications to the illustrated safety device and alternative forms of device will occur to those readers skilled in the art.

What is claimed is:

1. A securing device to be fixed externally to the body of a patient fitted with a surgical body tube for securing the body tube against unintentional displacement into or out of the patient, said device comprising tubular means having an axial bore for the body tube to pass through, a flexible elongated gripping element mounted within and extending generally longitudinally of said axial bore means securing said gripping element to said tubular means, and selectively adjustable means for helically winding said gripping element about the axis of said bore and the body tube passing through the bore for urging the element radially whereby to grip the body tube securely, said adjustable means being operable to also unwind said element to release the body tube and allow the latter to be pulled freely through the device.

2. A securing device as set forth in claim 1 wherein said elongated flexible gripping element includes a plurality of strips which are spaced circumferentially around the periphery of said bore and which are integrally attached to each other at said ends of the element.

3. A securing device as set forth in claim 1 wherein said tubular means comprises a pair of tubular members which are rotatable relative to each other about the bore axis, said gripping element having opposite ends fixed to the respective tubular members whereby said gripping element is twisted and untwisted about the bore axis in response to relative rotation of said tubular members.

4. A securing device as set forth in claim 3 wherein releasable locking means are provided for locking said tubular members positively against relative rotation in a direction to untwist the gripping element from its twisted tube gripping condition.

5. A securing device as set forth in claim 4 wherein said locking means are operable to permit relative rotation of the tubular members in the direction of twisting the element and tightening the grip thereof on the body tube, said locking means being also operable to release said members to permit relative rotation thereof in a direction to untwist the element and thereby release the tube.

6. A securing device as set forth in claim 5 wherein said locking means comprises ratchet structure including respective, cooperating ratchet teeth on the tubular members.

7. A securing device as set forth in claim 6 wherein the tubular members have axially opposed surfaces, the ratchet teeth being formed on said opposed surfaces, said ratchet teeth being disengageable to release the locking means by pulling the tubular members apart axially.

8. A securing device as set forth in claim 7 wherein said ratchet teeth are normally urged into cooperating engagement by tension of said gripping element.

9. A securing device as set forth in claim 3 wherein the tubular members are telescoped together and define said through bore.

* * * * *